United States Patent [19]

Gelperin

[11] Patent Number: 5,675,070
[45] Date of Patent: Oct. 7, 1997

[54] OLFATORY SENSOR IDENTIFICATION SYSTEM AND METHOD

[75] Inventor: Alan Gelperin, Princeton, N.J.

[73] Assignee: NCR Corporation, Dayton, Ohio

[21] Appl. No.: 599,572

[22] Filed: Feb. 9, 1996

[51] Int. Cl.$^6$ ................................................ G01N 33/497
[52] U.S. Cl. .................................................. 73/23.34
[58] Field of Search .................... 73/23.34, 431; 422/88, 83

[56] References Cited

U.S. PATENT DOCUMENTS

| | | | |
|---|---|---|---|
| 3,428,892 | 2/1969 | Meinhard | 73/23.34 |
| 3,942,357 | 3/1976 | Jenkins | 73/23 |
| 4,111,036 | 9/1978 | Frechette et al. | 73/23 |
| 4,476,169 | 10/1984 | Nishino et al. | 428/34 |
| 4,770,027 | 9/1988 | Ehara et al. | 73/23.34 |
| 4,909,089 | 3/1990 | Achter et al. | 73/863.11 |
| 4,909,090 | 3/1990 | McGown et al. | 73/864.33 |
| 5,047,214 | 9/1991 | Fukui et al. | 422/88 |
| 5,066,466 | 11/1991 | Hölter et al. | 422/98 |
| 5,123,274 | 6/1992 | Carroll et al. | 73/1 G |
| 5,177,994 | 1/1993 | Moriizumi et al. | 73/23.34 |
| 5,227,037 | 7/1993 | Suzuki et al. | 204/153.17 |
| 5,269,169 | 12/1993 | Trenkle et al. | 73/23.24 |
| 5,400,641 | 3/1995 | Slemon et al. | 73/19.01 |
| 5,426,071 | 6/1995 | Summers | 437/203 |
| 5,479,815 | 1/1996 | White et al. | 73/23.3 |
| 5,554,273 | 9/1996 | Demmin et al. | 205/785 |

OTHER PUBLICATIONS

*Sensor Array Recognition of Varieties of a Same Wine,* by Corrado Di Natale et al., pp. 711–714, Transducers '95.
*Screening of Irradiate Tomatoes by Means of an Electronic Nose,* by Fredrik Winquist, et al., pp. 691–694, Transducers '95.

*Sensors and Sensory Systems for an Electronic Nose,* by Julian W. Gardner et al., NATO ASI Series, Series E: Applied Sciences—vol. 212.

*Gas Identification Using Oxide Semiconductor Gas Sensor Array and Neural-Network Pattern Recognition,* by Hyung–Ki Hong, et al., pp. 687–690, Transducers '95.

*Analysis of Complex Gas Mixtures by Pattern Recognition with Polymer Based Quartz Microbalance Sensor Arrays,* Gerolf Kraus et al., pp. 675–678, Transducers '95.

Primary Examiner—Hezron E. Williams
Assistant Examiner—Jay L. Politzer
Attorney, Agent, or Firm—Matthew J. Hodulik; Paul W. Martin

[57] ABSTRACT

An artificial olfactory system and associated method for rapidly identifying an object by its aroma. The artificial olfactory system includes a testing chamber in which is disposed an array of gas sensors. The object to be identified is placed in close proximity to the testing chamber. The air pressure within the testing chamber is then lowered below ambient, thereby causing ambient air to flow past the object being identified and into the testing chamber. As air flows past the object being identified, the aroma of the object becomes mixed with the air and is carried into the testing chamber. Once within the testing chamber, the aroma/air mixture is exposed to the array of gas sensors. The gas sensors detect the levels of various gases comprising the aroma/air mixture and produce a sensor pattern capable of being identified using pattern recognition techniques.

12 Claims, 1 Drawing Sheet

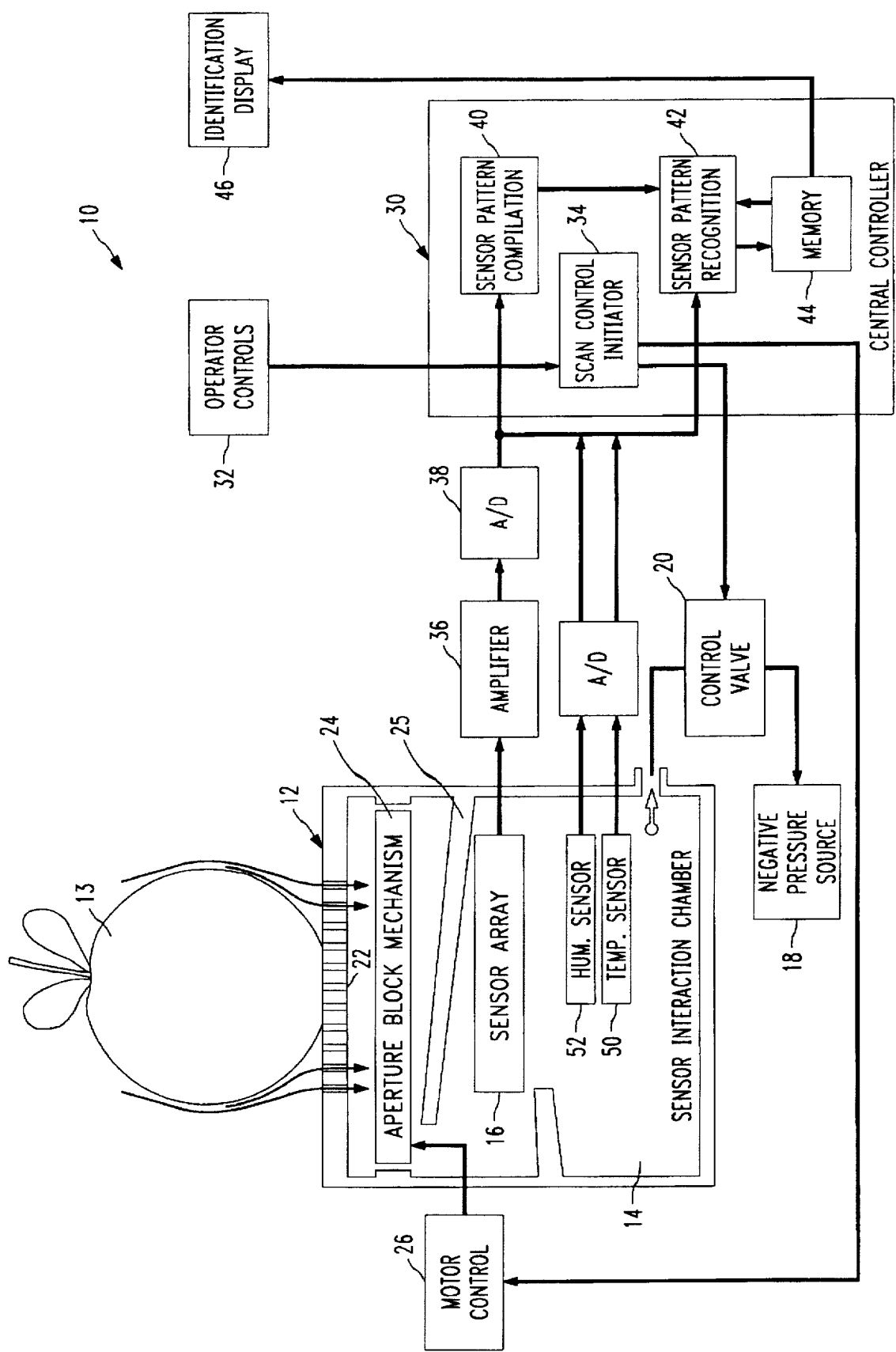

OLFATORY SENSOR IDENTIFICATION SYSTEM AND METHOD

BACKGROUND OF THE INVENTION

1. Field of the Invention

The present invention relates to artificial olfactory systems that use gas sensor arrays to identify an object by the odor emitted by that object. More specifically, the present invention relates to artificial olfactory systems and methods that receive air from around an object to be identified and direct the air to a gas sensor array, thereby enabling the system to identify a variety of different objects.

2. Prior Art Statement

Artificial olfactory systems, sometimes referred to as electronic noses, utilize an array of gas sensors to detect the concentration of various gases being emitted by an object or composition. The aroma or scent of an item is typically unique to that item and serves as an olfactory fingerprint that can be used to identify that item. The aroma of an item is comprised of various gases mixed together in a unique combination. By exposing the aroma of an item to a gas sensor array, the concentrations of the various gases comprising the aroma can be quantified. By matching the detected gas concentrations to known standard models, the item can be identified.

In the prior art, artificial olfactory systems are commercially available. The three largest manufacturers of such systems are Neotronics of Hertfordshire, Great Britain, ALPHA M.O.S., Inc. of DeMotte, Ind. and Aromascan Inc. of Hollis, N.H. Commercial artificial olfactory systems are widely used by industry to provide quantifiable quality control parameters to aromatic products. For example, artificial olfactory systems are used by industry to identify if one batch of perfume smells the same as previous lots or if cheese has aged to the proper degree. With items such as perfume, wine and cheese that have strong aromas, the human nose is typically not sensitive enough to detect minor anomalies in the aromas from day to day. However, by using artificial olfactory systems, the aroma of these items can be quantified and scientifically analyzed. As such, minor anomalies can be detected and a higher degree of quality control can be maintained. Two examples of artificial olfactory systems being used to quantify the aroma of consumer products can be found in the following articles: *SENSOR ARRAY RECOGNITION OF VARIETIES OF A SAME WINE* by DiNatale et al., 8th International Conference on Solid-State Sensors and Actuators, and Eurosensors IX, Stockholm, Sweden June (1995); and *SCREENING OF IRRADIATED TOMATOES BY MEANS OF AN ELECTRONIC NOSE*, by Winquist et al., 8th International Conference on Solid-State Sensors and Actuators, and Eurosensors IX, Stockholm, Sweden June (1995).

Commercial artificial olfactory systems currently available typically contain sample vessels into which the object to be tested is placed. The sensor array is then placed over the sample vessel. To begin a test, an aperture between the sample and the sensor array is opened. No movement of the air within the sample vessel is provided. Rather, such prior art artificial olfactory systems depend upon natural diffusion, wherein the aroma of the sample eventually fills the vessel and is detected by the sensor array. Such prior art artificial olfactory systems typically require a test period in the order of a few minutes. A testing time of a few minutes works well for companies that use artificial olfactory systems for quality control. When testing a batch of perfume, wine or cheese, time is not of the essence and a test that takes several minutes to complete is more than adequate. Furthermore, in testing items that have strong aromas, such as perfume, wine and cheese, there is little concern that within the test period of a few minutes, the aroma will diffuse through the testing chamber and adequate exposure will be provided to the sensor array.

There exist many applications where the identification of items by an artificial olfactory system would be beneficial, however such applications may require identification on a scale of a few seconds rather than on a scale of a few minutes, thereby eliminating the use of traditional slow artificial olfactory systems. For example, in a grocery store, a customer may come to the cashier's counter with apples. The apples are not individually labeled, so it is difficult for the cashier to determine what type of apple is being bought. Since different types of apples have different prices, the cashier must determine the type of apple before the customer can pay for the apples. If an artificial olfactory system were available, the apples could be identified by their smell. However, such an artificial olfactory system would have to work rapidly and provide an identification in a matter of seconds rather than the current prior art testing rate which may take several minutes.

Another application for an artificial olfactory system with a rapid response time would be at airport baggage inspection stations. At such inspection stations, pieces of luggage could be inspected by their aroma, thereby providing a means of detecting illegal drugs, explosives or other contraband. In such an application, the olfactory inspection would have to be complete in a matter of seconds for each piece of luggage.

A need therefore exists in the art for an artificial olfactory system and method that can identify a wide variety of items in rapid succession, wherein the time required to identify any one item would only take a few seconds.

SUMMARY OF THE INVENTION

The present invention is an artificial olfactory system and associated method for rapidly identifying an object by its aroma. The artificial olfactory system includes a testing chamber in which are disposed an array of gas sensors. The object to be identified is placed in close proximity to the testing chamber. The air pressure within the testing chamber is then lowered below ambient, thereby causing ambient air to flow past the object being identified and into the testing chamber. As air flows past the object being identified, the aroma of the object becomes mixed with the air and is carried into the testing chamber. Once within the testing chamber, the air/aroma mixture is exposed to the array of gas sensors. The gas sensors detect the levels of various gases comprising the air/aroma mixture and produce a sensor pattern that represents the various gas concentrations detected. The flow of air into the testing chamber is controlled both in volume and time. The drawing of air into the test chamber is preferably performed in less than two seconds. In this short amount of time, the flow volume is maintained at a level where the array of gas sensors is exposed to a volume of test air sufficient enough to make a reliable test.

As the array of gas sensors detects the composition of the air/aroma mixture, a sensor pattern is created that represents the object to be identified. Pattern recognition techniques are employed to match the newly generated sensor pattern to a known sensor pattern stored in memory. When a match between patterns is found, the object in question has been identified. The pattern recognition techniques used preferably select a match within two seconds of processing time.

As a result, the combined time to draw the test air into the test chamber and analyze the results only takes a few seconds. Such a rapid identification time makes the present invention artificial olfactory system applicable to situations where a variety of diverse objects must be identified quickly, such as at cashier check-out counters, mail sorting rooms and airport baggage inspection stations.

BRIEF DESCRIPTION OF THE DRAWINGS

For a better understanding of the present invention, reference is made to the following description of an exemplary embodiment thereof, considered in conjunction with the accompanying drawing, in which:

FIG. 1 is a block diagram schematic of one preferred embodiment of the present invention, illustrating both the components of an artificial olfactory device and its method of operation.

DETAILED DESCRIPTION OF THE INVENTION

Although the present invention artificial olfactory system and method can be used in a wide variety of applications, such as detecting drugs or explosives in luggage or packages, the present invention system and method are particularly well suited for use in identifying produce at a cashier's counter. Accordingly, the present invention artificial olfactory system and method will be described in an application involving a cashier's counter as the exemplary embodiment.

Referring to FIG. 1, a preferred embodiment of the present invention artificial olfactory system 10 is shown containing a produce scan surface 12. The produce scan surface 12 is preferably positioned at the cashier's station and may be either an independent unit or may be built into the cashier's counter, as are traditional bar code scanners. The produce scan surface 12 covers a sensor interaction chamber 14, in which is disposed at least one sensor array 16. The produce scan surface 12 is perforated, thereby enabling the aroma of a piece of produce 13 placed on the produce scan surface 12 to be drawn into the sensor interaction chamber 14, as will later be explained. A negative pressure source 18 is connected to the sensor interaction chamber 14, wherein the negative pressure source 18 is selectively isolated from the air within the sensor interaction chamber 14 by a control valve 20. As would be understood, "negative pressure", as utilized herein, generally represents a pressure below that of ambient pressure.

When the control valve 20 is open, the negative pressure source 18 draws the air out of the sensor interaction chamber 14, thereby producing a negative pressure within the sensor interaction chamber 14. The negative pressure within the sensor interaction chamber 14 causes air to flow into the sensor interaction chamber 14, past the produce 13 and through the apertures 22 in the produce scan surface 12. As a result, the aroma of the produce 13 on the produce scan surface 12 is actively drawn into the sensor interaction chamber 14, wherein the drawn air is received by the sensor array 16. By using the negative pressure source 18 to draw the aroma of the produce 13 into the sensor interaction chamber 14, the artificial olfactory system 10 in essence sniffs the produce 13 to optimize the sampling of the aroma by the sensor array 16 in a highly time efficient manner. By drawing the aroma of the produce 13 into the sensor interaction chamber 14 in about one second, the sensor array 16 experiences a concentration of aroma that would take minutes to obtain by a prior art artificial olfactory system where no air flow is provided.

The sensor interaction chamber 14 can be positioned at any point above, below or to the side of the produce 13 being tested, provided the air drawn into the sensor interaction chamber 14 is drawn past the produce 13. In the shown embodiment, the sensor array 16 is positioned below the produce 13. In such an orientation, it is highly desirable to protect the sensor array 16 from debris, condensate, juices or other contaminants that may fall from the produce 13. As a result, a contaminant shield 25 is provided within the sensor interaction chamber 14 that protects the sensor array 16 from any contaminants that may fall through the apertures 22 in the produce scan surface 12. The contaminant shield 25 is disposed between the sensor array 16 and the produce scan surface 12, preventing falling debris from contacting the sensor array 16. The contaminant shield 25 also acts as an air flow baffle, helping to mix the incoming air and direct the incoming air toward the sensor array 16. The containment shield 25 should be easily removable or accessible to enable a person to periodically clean the contaminant shield 25 and keep the contaminant shield 25 odor free.

To prevent the contamination of the sensor array 16 from airborne contaminants, an aperture block mechanism 24 can also be optionally provided. The aperture block mechanism 24 can be any mechanism capable of selectively obstructing the apertures 22 in the produce scan surface 12, thereby isolating the sensor array 16 within the sensor interaction chamber 14. In the shown embodiment, the aperture block mechanism 24 includes a motor control 26, wherein the operation of the motor control 26 causes the aperture block mechanism 24 to selectively open and close. When the aperture block mechanism 24 is open, air from around the produce 13 is capable of being drawn into the sensor interaction chamber 14. Conversely, when the aperture block mechanism 24 is closed, the contents of the sensor interaction chamber 14 are isolated from the surrounding ambient environment.

The operation of the artificial olfactory system 10 is controlled by a central controller 30 which may be a dedicated unit or a programmable unit such as a personal computer. During operation, the cashier places a piece of produce 13 onto the produce scan surface 12. Using operator controls 32 available to the cashier, the cashier then initiates one cycle of operation for the artificial olfactory system 10. A scan control initiator 34 within the central controller 30 operates the aperture block motor control 26 and opens the aperture block mechanism 24 so that the apertures 22 below the produce 13 communicate with the sensor interaction chamber 14. The scan control initiator 34 also opens the control valve 20 for a brief active testing period of between 0.5 seconds and 5 seconds, with the preferred duration being between one and two seconds. During the testing period when the control valve 20 is open, air is drawn into the sensor interaction chamber 14 for analysis. At the end of the brief testing period, the control valve 20 is closed and the aperture block motor control 26 is directed to close the aperture block mechanism 24 and again obstruct the apertures 22 in the produce scan surface 12.

During the brief testing period when air is drawn past the produce 13 and into the sensor interaction chamber 14, the sensor array 16 is exposed to a fairly large volume of air containing the aroma of the produce 13 placed upon the produce scan surface 12. The sensor array 16 contains a plurality of gas sensors, wherein each of the gas sensors is designed to detect a specific type of gas or combination of gases. In the shown embodiment of a produce identifier, the gas sensors in the sensor array 16 are selected to detect the gases commonly found in the aromas of produce. Gas sensors capable of detecting non-organic gases would therefore not need to be used. However, in alternate applications such as drug detection or explosives detection, the gas sensors within the sensor array would be selected to be most sensitive to the materials being sought.

The prior art is replete with gas sensors that are sensitive to different gases. Textbooks are even available on the subject as exemplified by the book SENSORS AND SENSORY SYSTEMS FOR AN ELECTRONIC NOSE, by Julian Gardner and Philip Bartlett, Kluwer Academic Publishers (1992). As such, the composition of the gas sensors for use in the sensor array 16 need not be set forth herein. The gas sensors selected for the sensor array 16 are selected to detect the range of gases commonly associated with produce 13. The gas sensors contained within the sensor array 16 therein produce an analog signal in response to the aroma filled air impinging upon the sensor array 16 within the sensor interaction chamber 14. The sensor arrays used in prior art artificial olfactory systems typically have a slow steady state response that works well given the long testing periods required by such prior art devices. In the shown embodiment oft he artificial olfactory system 10, an amplifier stage 36 is provided to amplify the analog signals generated by the gas sensors in the sensor array 16. The amplifier stage 36 serves two purposes. First, the amplifier stage 36 strips the analog gas sensor signals of the steady state response. Second, the amplifier stage embodies a high frequency cutoff filter. Conducting polymer gas sensors, such as those preferably used in the sensor array 16, are unlikely to respond on a time scale less than ten milliseconds. As such, an amplifier stage responsive to high frequencies would introduce noise into the analog signal. The use of a high frequency cutoff filter embodied within the amplifier stage 36, thereby prevents such noise from being experienced by the system.

The amplifier stage 36 enables a fast transient response, produced by the gas sensors, to be isolated. The amplified analog signal for each of the gas sensors in the sensor array 16 is converted to corresponding digital signals by an analog-to-digital converter 38. The digital signals are read by the central controller 30, wherein the central controller 30 compiles an overall sensor pattern for the produce 13 being scanned, as is indicated by block 40. The sensor pattern generated for the produce 13 represents the olfactory fingerprint for that piece of produce. As is indicated by block 42, after a sensor pattern is generated, pattern recognition techniques are applied to the sensor pattern, wherein the sensor pattern is compared to sensor patterns stored in a memory 44. If a match is found between the sensor pattern in question and a known sensor pattern from memory 44, the produce 13 has been positively identified. The identity of the produce 13 can then be viewed by the cashier at a display 46 and/or the produce's identity can be read directly into the cashier's register.

Techniques for identifying the sensor pattern produced by a gas sensor array by using pattern recognition techniques are well known in the art. Examples of articles illustrating such pattern recognition techniques include GAS IDENTIFICATION USING OXIDE SEMICONDUCTOR GAS SENSOR ARRAY AND NEURAL-NETWORK PATTERN RECOGNITION by Hong et al., 8th International Conference on Solid-State Sensors and Actuators, and Eurosensors IX, Stockholm, Sweden (1995); and ANALYSIS OF COMPLEX GAS MIXTURES BY PATTERN RECOGNITION WITH POLYMER BASED QUARTZ MICROBALANCE SENSOR ARRAYS, by Kraus et al., 8th International Conference on Solid-State Sensors and Actuators, and Eurosensors IX, Stockholm, Sweden (1995). Any such prior art pattern recognition technique can be used in conjunction with the present invention artificial olfactory system 10.

In FIG. 1, it can be seen that an optional temperature sensor 50 and humidity sensor 52 can be placed within the sensor interaction chamber 14. Many types of polymer coated quartz microbalance gas sensors, such as those preferably used within the sensor array 16, are sensitive to both changes in humidity and changes in temperature. The temperature and humidity of a grocery store remain fairly constant from hour to hour. However, the environmental stability of the ambient air does not translate into environmental stability within the sensor interaction chamber 14. Some produce is stored at ambient temperature. However, other produce is stored at refrigerated temperatures and may be periodically misted with water. When a refrigerated piece of produce 13 is placed on the produce scan surface 12, the produce 13 may be damp and/or condensation may form on the produce 13. As a result, when air is drawn past the produce 13 and into the sensor interaction chamber 14, the air would be colder and more humid than ambient air. As a result, the sensitivity of the sensor array 16 would change and the sensor pattern would change. The sensor pattern for a cold head of lettuce may therefore be significantly different from a head of lettuce at ambient temperature.

In the shown embodiment, the analog signals from the temperature sensor 50 and humidity sensor 52 are converted to digital signals and are read by the central controller 30. The central controller 30 can then modify the sensor pattern generated in view of temperature and/or humidity, prior to the sensor pattern being subjected to pattern recognition. As a result, the sensor pattern of a cold head of lettuce would be modified by the central controller 30 to be generally the same as that of a head of lettuce at ambient temperature. Alternatively, the memory 44 of sensor patterns stored by the central controller 30 may contain a plurality of sensor patterns for each different type of produce, wherein several of the sensor patterns represent the same piece of produce but at different temperatures and/or humidity levels. During pattern recognition, the central controller 30 then matches the subject sensor pattern to the closest memory sensor pattern without having to alter the subject sensor pattern to compensate for temperature and humidity changes.

In an effort to further improve the accuracy of identifications, the present invention olfactory system may be enabled to periodically establish a baseline or reference reading for the background odors surrounding the scan surface absent any objects to be identified. These background odors may include, for example, perfume or cologne worn by a checkout person or customer. By establishing an initial background reference pattern for the scanning environment prior to making actual identifications, the system is enabled to compensate for those odors already existing in the scan environment. In order to compensate for the background odors, the controller may then perform a subtraction of the background odor prior to comparison of the scan pattern of an object to be identified with a reference pattern. As would be understood, the background odor scan can be periodically adjusted, either automatically and/or as a manual operation in order to ensure accurate identifications of produce or other objects.

It will be understood that the embodiment of the present invention described above is merely exemplary and many aspects of the exemplary embodiment can be modified by a person skilled in the art. All such modifications are intended to be covered by the scope of this disclosure as set forth in the appended claims.

What is claimed is:

1. A device for identifying a produce item by its aroma to facilitate its purchase, comprising:

a housing defining a chamber at a checkout counter including a surface having an aperture;

an array of sensors disposed within said chamber for determining at least part of a composition of the aroma, wherein said array of sensors produces a sensor pattern for the aroma; and negative pressure means, coupled to said chamber, for lowering pressure within said chamber and causing air to be drawn into said chamber through the aperture in the surface and past the produce item when the produce item is placed adjacent the aperture, wherein the air drawn into said chamber carries the aroma of the produce item and exposes the aroma to said array of sensors for analysis; and a pattern recognition system, coupled to said array of sensors, including a controller for identifying the aroma by comparing the sensor pattern to a reference sensor pattern.

2. The device according to claim 1, further including a flow control valve, disposed between said housing and said negative pressure means, for selectively regulating air flow between said chamber and said negative pressure means.

3. The device according to claim 2, wherein said controller opens said flow control valve for a time period of between 0.5 seconds and 5.0 seconds, thereby enabling the aroma from the produce item to be drawn into said chamber and exposed to said array of sensors for the duration of said time period.

4. The device according to claim 1, wherein said sensor pattern produced by said array of sensors varies with temperature and said device further includes a temperature sensor, disposed within said chamber and coupled to said pattern recognition system, for providing said pattern recognition means with the temperature at which said sensor pattern was produced.

5. The device according to claim 1, further including a closure means for selectively blocking the aperture in the surface and isolating said chamber, wherein said closure means blocks the aperture at all times other than during said time period when the aroma of the produce item is drawn into said chamber.

6. The device according to claim 1, wherein said sensor pattern produced by said array of sensors varies with humidity and said device further includes a humidity sensor, disposed within said chamber and coupled to said controller, for providing said controller with the humidity at which said sensor pattern was produced.

7. A method of identifying a produce item by its aroma to facilitate its purchase, comprising the steps of:

providing a housing defining a chamber at a checkout counter including a surface having an aperture, wherein the chamber contains a sensor array;

positioning the produce item adjacent the aperture in the housing;

lowering air pressure within said chamber during a time period so that the aroma of the produce item is drawn into said chamber;

producing a sensor pattern for the aroma using said sensor array; and matching said sensor pattern to a known sensor pattern.

8. The method according to claim 7, wherein said time period is between 0.5 seconds and 5.0 seconds.

9. The method according to claim 7, further including the step of measuring the temperature within said chamber during said time period and altering said sensor pattern to compensate for temperature.

10. The method according to claim 7, wherein said step of lowering includes the substeps of joining said chamber to a low pressure source and selectively opening a valve positioned between said low pressure source and said chamber.

11. The method according to claim 7, further including the step of isolating said chamber from the ambient environment at times other than said time period.

12. The method according to claim 7, further including the step of measuring the humidity within said chamber during said time period and altering said sensor pattern to compensate for humidity.

* * * * *

UNITED STATES PATENT AND TRADEMARK OFFICE
CERTIFICATE OF CORRECTION

PATENT NO. : 5,675,070
DATED : October 7, 1997
INVENTOR(S) : Alan Gelperin

It is certified that error appears in the above-indentified patent and that said Letters Patent is hereby corrected as shown below:

Title Page, after [54] delete "OLFATORY" and substitute --OLFACTORY--.

Title page, col. 1, line 1, delete "OLFATORY" and substitute -- OLFACTORY__.

Signed and Sealed this

Seventh Day of March, 2000

Attest:

Attesting Officer

Q. TODD DICKINSON

Commissioner of Patents and Trademarks